United States Patent [19]

Olsen et al.

[11] Patent Number: 4,853,335

[45] Date of Patent: Aug. 1, 1989

[54] COLLOIDAL GOLD PARTICLE CONCENTRATION IMMUNOASSAY

[76] Inventors: Duane A. Olsen, 7619 44 West No. 2, Tacoma, Wash. 98466; David Bernstein, 5814 Melville Rd., Sykesville, Md. 21784

[21] Appl. No.: 101,415

[22] Filed: Sep. 28, 1987

[51] Int. Cl.$^4$ .................. G01N 33/543; G01N 33/544
[52] U.S. Cl. .................................... 436/527; 436/525; 436/528; 436/530; 436/535; 436/807; 435/7; 435/805; 422/56; 422/60
[58] Field of Search ............... 436/523, 525, 528, 530, 436/535; 435/7; 422/56, 60

[56] References Cited

U.S. PATENT DOCUMENTS

| | | | |
|---|---|---|---|
| 4,313,734 | 2/1982 | Leuvering | 436/525 |
| 4,373,932 | 2/1983 | Gribnau | 436/538 X |
| 4,459,361 | 7/1984 | Gefter | 436/523 |
| 4,552,839 | 11/1985 | Gould | 435/7 |
| 4,703,017 | 10/1987 | Campbell | 436/525 X |
| 4,745,075 | 5/1988 | Hadfield | 436/523 |

FOREIGN PATENT DOCUMENTS

WO/8505451 12/1985 PCT Int'l Appl. .

OTHER PUBLICATIONS

J. Imm. Methods, vol. 74, Moeremans et al, "Sensitive Visualization of Ag-Ab Reactions in Dot & Blot Immune Overlay Assays with Immunogold & Immunogold/Silver Staining", pp. 353–360, 1984.

Primary Examiner—Christine M. Nucker
Assistant Examiner—Karen I. Krupen

[57] ABSTRACT

A sandwich immunoassay method is disclosed that is useful for the identification of an antigen in biological specimens. The method is comprised of a colloidal gold labeled binder specific for epitopes or receptors of a ligand, nonporous particulate solid phase which have antiligand covalently attached, and which said reagents are combined with the biological specimen or an extract of the biological specimen, and after an appropriate incubation, the said reactant mixture is contacted to a porous film having an exposed surface area of contact no greater than 30 mm$^2$ to separate and concentrate the particle bound colloidal gold labeled binder from the unbound. The identification of an antigen is determined by the presence of color on the surface of the solid phase particles captured on the surface of the film. A competitive inhibition assay can be also used to identify the presence of a hapten or antigen, in which case the presence of the analyte is determined by the absence of color.

27 Claims, No Drawings

COLLOIDAL GOLD PARTICLE CONCENTRATION IMMUNOASSAY

BACKGROUND OF THE INVENTION

1. Field of Invention

The invention relates to a colloidal gold sandwich immunoassay method for the identification of antigen or hapten analytes in biological specimens. More particularly, the invention relates to an immunological method for analyzing biological fluids wherein the separation and concentration of solid phase bound colloidal gold labeled binder is conducted on a finite area of a porous film wherein the reaction can be visualized by the human eye.

2. Discussion of Prior Art

Immunodiagnostic testing is rapidly evolving toward more simplistic approaches in the rapid identification and diagnosis of disease states. There is often a need for a simplistic qualitative assay to detect the presence or absence of an analyte in a clinical specimen including viral, bacterial, fungal associated antigens, tumor markers, cell surface markers, drugs, hormones, and the like derived from clinical specimens such as blood, plasma, serum, cerebrospinal fluid, lymph or tissue fluid, wounds, pus, cells, tissue biopsies, urine or fecal material, swabs or lavages of the urogential, nasopharyngeal, anal, and conjunctival areas of the body.

In addition, as the testing facility is at satellite laboratories, physicians offices, or the home, the existence and performance of a noninstrumented simple assay is desirable, especially where a poorly trained or lay person may perform the test. Noninstrumented immunoassay systems are not capital intensive and can have greater utility and flexibility away from the clinical laboratory. Improvements in simplicitity, speed, specificity, and sensitivity have been ongoing challenges to those individuals involved in developing diagnostic test kits.

The methodologies for noninstrumented qualitative or semi quantitative sandwich immunoassay techniques have included enzyme immunoassays such as those described in 1971 by Engvall and Perlmann in Immunochemistry 8: 871 and Van Weeman and Schuurs in FEBS lett. 15: 232. Further development of sandwhich enzyme immunoassays with chromogenic substrate developed on the surface of a ligand or antiligand coated porous membrane, paper, strip, or film were described by Valkirs et al in U.S. Pat. No. 4,632,901 (1986) and by Frickey et al in U.S. Pat. No. 4,670,381 (1987). Nonenzyme labeled assays on bibulous paper using dyed particles as labels were disclosed by Gould et al in U.S. Pat. No. 4,552,839 (1985). The use of colloidal gold labeled antibodies in an immunoassays were reported by Horrisberger et al in 1977 in Journal of Histochem & Cytochem 25: 295. Horrisberger describes a gold sol immunoassay for mannan wherein there is a change in light absorption upon the aggregation of colloidal gold labeled antibodies. A similar metal sol particle immunoassay is described by Leuvering in U.S. Pat. No. 4,313,734 (1982). In addition Leuvering discloses a sandwich gold sol immunoassay wherein antibody coated plastic plates are coated with specific antibody, followed by the addition of test sample, and incubated. The plate is then washed, gold labeled anti ligand antibody is added, and again incubated. The plate is washed again, and an eluting buffer is added to elute the bound colloidal gold and then read spectrophotometrically. Cerny in patent application #8,502,534 discloses the use of colloidal gold as a label for antibodies in a sandwich assay wherein the bound and unbound labeled antibodies or antigens are separated on an antibody coated porous membrane through radial diffusion. Jolley et al describe a particle concentration fluorescence immunoassay in J. Immunol. Meth (1984) 67: 21 wherein a sandwich assay is performed using antibody coated particles, fluorescent labeled antibodies and a filtration membrane which captures and concentrates the coated particles and bound fluorescent dye which is washed and then measured by front surface fluorometry.

Gefter in U.S. Pat. No. 4,459,361 (1984) discloses a ligand assay with one or two particulate reagents and filter, wherein agglutinated antibody coated dyed particles are separated from nonagglutinated particles by use of a controlled pore size membrane filter. Edwards et al disclose in U.S. Pat. No. 4,666,863 (1987) an immunoassay with chromatographic medium and labeled reagent wherein specific binder for an analyte is attached to solid phase particles. The particles are chosen so that when applied to a spot on a flat sheet chromatographic medium, they do not migrate to any significant extent under the influence of a subsequent applied solvent, while the unbound labeled reagent migrates away from the spot.

The potential of separating bound and unbound labeled materials by attaching one component of reactants to particles and capturing the particles by either diffusion, filtration, capillary action, or chromatography in which the solid phase particles remain immobilized is now well known to those skilled in the art. However, the labels used are of a nature that because of nonspecific interactions, washing steps are required for separation of the bound and unbound label. In addition all of these solid phase particles assays suffer from the following drawbacks required of a simple immunoassay system:

1. There are too many steps for those assays which utilize enzymes, requiring at least one washing step and or addition of a substrate reagent, and the timing of reading is critical.

2. Those assays which require some kind of instrumentation for reading such as in the case of a fluorescent dye are unsuitable for many testing sites.

3. Those assays which require sequential additions of reagents, as in standard enzyme immunoassay procedures, are more difficult to perform, time consuming, and more costly to manufacture multiple reagents.

4. Those assays performed on ligand or antiligand coated porous films, filter, or membranes must be prepared specifically for each particular analyte to be tested and because of limited surface area and reaction time with antigens, this methodology may be inappropriate if the affinity of the antiligand for the ligand is low.

SUMMARY OF THE INVENTION

The object of the present invention is to overcome the shortcomings of existing noninstrumented sandwich immunoassays by providing a method and reagents wherein a qualitative or semiquantitative immunoassay can be performed easily, with a minimum number of steps and reagent containers, in addition to being easy to read, sensitive and specific.

The present invention is a sandwich immunoassay which utilizes a colloidal gold labeled ligand or antiligand reagent and ligand or antiligand bound solid phase particles and which the aforesaid reagents are combined prior to or simultaneously with an aqueous extract of a sample or an aqueous sample. The reactants are incubated and subsequently allowed to flow into an exposed area no greater than 30 mm² of a porous film by the process of diffusion, chromatography, positive or negative filtration, or any combination thereof, and wherein the pore size of the porous film is such that the solid phase particles are retained on the surface of the film, and large enough that the unbound colloidal gold labeled reagents pass through easily. The particles captured on the membrane are visually inspected for color and a determination of the presence or absence of an analyte is made.

DESCRIPTION OF THE SPECIFIC EMBODIMENTS

The subject invention is based on the concentration of ligand or antiligand bound solid phase particles into a small area less than 30 mm² of a porous film and the separation at this interface of bound and unbound colloidal gold labeled ligand or antiligand reagent. The test sample can be derived from a biological specimen, and if the analyte of interest in the specimen is associated with or is in the presence of particles that would not pass through the porous film, the specimen can be extracted to solubilize or expose reactive epitopes of the ligand and or prefiltered to remove any debirs prior to any reaction with the ligand or antiligand bound solid phase particles.

The choice of solid phase particles should be of a material that is nonporous to the colloidal gold labeled reagent. The shape of the particles are not critical, but the mean particles sizes should be such that a large reactive surface area can be obtained to maximize the reaction kinetics and at the same time allow for maximum capturing of the particles on the membrane with a minimal amount of layering that might hamper reading the maximal signal derived from the concentrated solid phase bound colloidal gold reagent. Choices of materials for the solid phase particles are extensive and include particles made from glass, acrylamide or methacrylate, nylon, polystyrene, dextrans, cellulose or any derivatives thereof. The choice of particles and the method of covalently or noncovalently attaching the ligand or antiligand to the selected particle are well known in the art. Other criteria for selecting the solid phase particles include that the particles should be white or almost colorless to easily differentiate the color of the colloidal gold label which can appear to the naked eye as a faint pink to an almost black. The particles could be fixed on the surface of the microporous film prior to the addition of the other reagents, but it is preferable that the solid phase particles are suspended in the reaction mixture to maximize the interactions through Brownian motion; and therefore the particles should have a size and density that allow for its suspension. Covalent attachment of ligand or antiligand is preferrable for stability reasons but not essential. The particles of choice are uniform polystyrene particles, generally called latex particles, which are commercially available as derivatized uniform latex spheres to make covalent attachment easy. Latex beads having a mean particle diameter size ranging from 0.10 to 20.0 microns, more usually from about 0.4 to 2.0 microns are preferred. The concentration of particles in the assay can range from 0.001% to 1.0%, more usually from about 0.005% to 0.2% weight per volume. The particles can be provided as a suspension or lyophilized with or without the labeled colloidal gold reagent.

The colloidal gold reagent is selected for its unusual properties: the ability to intensify color to the naked eye when concentrated on solid surfaces, the ability to minimally bind nonspecifically to solid surfaces, the ability to be prepared in relatively uniform particle sizes, and the ability to be easily lyophilized and reconstituted. Colloidal gold particles can be prepared in a number of ways through the reduction of chloroauric acid which produces a variety of particle sizes ranging from 5 nm to 100 nm. The preferred particle sizes are from 5.0 to 49 nm, usually from 10 to 20 nm. The colloidal gold particles can have an intermediary binder absorbed to its surface prior to the addition of the ligand or antiligand reagent, but direct attachment is satisfactory. Absorbing the selected ligand or antiligand is achieved by carefully controlling concentrations, ionic strength and pH of the reaction mixture. The choice of method of producing the colloidal gold raw material or the method of attaching the ligand or antiligand are well known to those skilled in the art. After the labeling with colloidal gold is complete, the reagent is differentially centrifuged and filtered to control particle size. Particle sizing by gel filtration methods are also well known. The colloidal gold labeled reagent can be used as a colloidal suspension or as a lyophilized reagent with or without the presence of the aforesaid solid phase particles as a single reagent.

The selection of the porous film is not critical and can be any material as those porous spreading layers, bibulous papers, filters, membranes, or chromatographic media described in U.S. Pat. Nos. 4670381, 4632901, 4666863, 4459361, 4517288, and 4552839 such as porous or fibrous materials composed singly or in combination of glass fibers, cellulose acetates, nylon, etc. The criteria of selection is that the material has controlled pore sizes ranging from 0.05 to 20.0 microns, usually ranging from 0.6 to 1.2 microns. The flow of the aqueous reagents can be controlled through diffusion, filtration, positive or negative pressure, and the membrane should have low nonspecific binding for the colloidal gold labeled reagent before or after treatment with reagents such as proteins, detergents, or salts. There are many porous membrane, films, or papers available commercially which have controlled hydrophobicity and are suitable for use in this invention. The porous film can be any shape and thickness but usually is flat and thin. The absorption, diffusion or filtration of the fluid phase of the reactants in the separation step can be facilitated by the addition of a fibrous or hydrophilic material in contact with the underside of the porous film. The size of the area exposed to the solid phase particles can be controlled by using a device comprised of a hydrophobic material such as plastic, plastic laminate, or other similar substance that is placed in contact with the porous film and seals the porous film such that only a surface area no greater than 30 mm² is exposed to the particulate solid phase. The size of the exposed surface area of the porous film is in the range of 0.2 to 30.0 mm², usually from 0.8 to 5.0 mm².

The preferred embodiment of the performing the present invention may vary according to the analyte in question. For example, where the analyte is a multivalent antigen and the test specimen is a fluid, the assay is performed by simultaneously incubating the colloidal gold labeled antiligand, antiligand coated solid phase particles, and the test specimen together for an appropriate time period, followed by separation of the bound and unbound gold labeled antiligand through and across the surface of the porous membrane film. If the specimen is of a particulate nature, such as tissues or cells, the particulates can be optionally solubilized with a solubilizing procedure known to those skilled in the art, such as enzymatic digestion, chaotropic or high salt concentrations, or detergent treatment followed by prefiltration or centrifugation. The assay can also be performed as a competitive inhibition assay, particularly where the analyte is a hapten in a biological fluid. In this case the assay is performed by simultaneously incubating the test fluid with colloidal gold labeled antiligand and hapten conjugate coated solid phase particles or incubating the test fluid with colloidal gold labeled hapten conjugate and antiligand coated solid phase particles. After appropriate incubation the bound and unbound colloidal gold labeled reagent is separated on the porous film. The absence of color on the surface of the solid phase particles after concentration on the film is indicative of the presence of the hapten in the specimen. Competitive assays can also be performed for antigens or antibodies and are well known to those skilled in the art. For example, in the case of a serological test wherein the specimen is plasma or serum and the analyte is an antibody, the specific target antigen can be attached to the solid phase particles and a specific antibody labeled to colloidal gold. After appropriate incubation with the test serum, the reaction mixture is separated on the surface of the porous film. The absence of color is indicative of the presence of antibody in the specimen which has competitively inhibited the binding of the labeled gold antibody to the antigen coated solid phase particles.

EXAMPLE I

Preparation and performance of a colloidal gold particle concentration immunoassay for Group A streptococci.

The pH of one hundred milliliters of colloidal gold (obtained from Janssen Pharmaceuticals) having a mean particle size of approximately 20 nm and an optical density of 1.2 at 520 nm was adjusted to 9.5 with 0.2M potassium carbonate. Variable isotherms for stabilization of colloidal gold sols with particular proteins and antigens are performed to find the optimal pH and concentrations. It was determined that 6 micrograms of affinity purified streptococcal antibody diluted to 100 micrograms per milliliter in 0.002M borax buffer pH 9.0 was the optimal amount to add per milliliter of colloidal gold solution. After absorption was allowed to proceed for ten minutes, the adsorption of the antibody was stopped by adding 10% bovine serum albumen (BSA) to a final concentration of 1%. The labeled colloidal gold was centrifuged at 16000 g for 30 minutes and resuspended in a buffer containing 0.02M tris pH 8.2, 1% BSA, and 0.05% sodium azide. The solution was centrifuged twice and resuspended into the same buffer to a final optical density at 520 nm to 1.5.

Five milliliters of a 10% suspension of carboxylated polystyrene particles (latex) having a mean particle size of 0.9 microns (obtained from Seragen, Indianapolis, IND) were activated with ethyldimethylaminopropylcarbodiimide (EDCI) as follows: The latex was centrifuged at 10000 g for 20 minutes, and resuspended in a solution of 400 mg of EDCI the pH was adjusted to 4.0 and allowed to react with mixing for 4 hours. The EDCI activated latex was subsequently centrifuged and the pellet was resuspended into 50 milliliters of 0.05M borate buffer pH 8.0 containing rabbit affinity purified antistreptococcal antibody at a concentration of 100 micrograms protein per milliliter. The antibody latex mixture was allowed to react with constant shaking for 18 hours. The mixture was centrifuged at 10000 g for 20 minutes and the latex pellet was resuspended into 50 milliliters of 0.1M glycine buffered saline pH 8.0. The latex was recentrifuged and resuspended to a final concentration of 0.1% weight per volume in 0.05M glycine buffered saline pH 8.0 containing 0.05% tween 20, 0.05% sodium azide.

Dacron throat swabs were seeded with 25 microliters of varying cell counts of Group A streptococci and Group C streptococci to evaluate the sensitivity and specificity of the test system as follows: Swabs were placed in a micronitrous acid extraction media to solubilize the Group A streptococcal polysaccharide. One hundred microliters of neutralized micronitrous acid extract was reacted with 50 microliters of the gold labeled reagent and 50 microliters of the solid phase particles. After incubating for 2 minutes, the reactants were placed on a 1.2 micron pore size cellulose acetate membrane covered with plastic laminate having circular orifices ranging in diameter from 1.0 to 5.0 mm. After the liquid phase absorbed by diffusion through the orifice, the color of the orifice was determined by the naked eye. The results are summarized in the following table:

| Number of organisms | Intensity of color at different orifice diameters in mm. | | | | | |
|---|---|---|---|---|---|---|
| | 1.0 | 1.5 | 2.0 | 3.0 | 4.0 | 5.0 |
| $10^6$ Group A strep | 3+ | 3+ | 3+ | 2+ | 1+ | 1+ |
| $10^5$ Group A strep | 3+ | 3+ | 2+ | 2+ | 1+ | N |
| $10^4$ Group A strep | 2+ | 2+ | 2+ | 1+ | N | N |
| $10^3$ Group A strep | N | N | N | N | N | N |
| $10^6$ Group C strep | N | N | N | N | N | N |

EXAMLE II

Preparation and performance of colloidal gold particle concentration immunoassay for *Neisseria gonorrhoeae*.

Hybrid cell producing monoclonal antibodies directed against principal outer membrane protein of *N. gonorrhoeae* were produced according to methods described by Tam et al in Infection and Immunity (1982) 36: 1042.

Monoclonal antibodies were screened in an ELISA test and selected for reactivity against different gonococcal and nongonococcal strains. The antibodies were purified on a Staphylococcal protein A sepharose adsorbant column. Each monoclonal antibody was treated in this manner before use in the making of a colloidal gold probe or a latex particle support.

Each of the selected mouse monoclonal antibodies were labeled with colloidal gold after determining the optimal protein concentration and optimal pH conditions for each antibody. Colloidal gold (Janssen pharmaceutical) 20 nm mean particle size diameter having an optical density at 520 nm of 1.2 was reacted with 6 to 10 micrograms of monoclonal antibody to each milliliter of colloidal gold reagent at pH ranging from 7.0 to 9.5 depending upon the isoelectric point of each antibody. After reacting the antibody and colloidal gold for two minutes, bovine serum albumen (BSA) was added to a final concentration of 1% and then the mixture was centrifuged at 10000 g for 30 minutes. The pellet was resuspended in 0.02M tris pH 8.2 containing 1% BSA and 0.05% sodium azide to a final optical density at 520 nm of 0.6. Mouse monoclonal antibodies specific for *N. gonorrhoeae* was covalently linked to carboxylated latex particles (0.9 micron, Seragen) by first activating 500 microliters of a 2.5% suspension of beads with an equal volume of 1M EDCI for 2 hours at room temperature. The beads were washed three times with 0.05M sodium chloride and subsequently resuspended in one milliliter of 0.05M sodium chloride pH 7.0. An equal volume of the same buffer containing 1 mg/ml monoclonal antibody protein was added to the activated beads for 12 hours. An equal volume of 0.5M ethanolamine at pH 7.5 was added for two hours at room temperature to block any unreacted sites. The mixture was centrifuged at 10000 g for 20 minutes and the pellet was washed three times with 0.02M sodium phosphate buffered saline containing 0.05% zwittergent and 0.05% sodium azide pH 7.5 to a final latex concentration of 0.6% weight/volume.

A known concentrations of $1.5 \times 10^9$ colony forming units (CFU)/milliliter of *N. gonorrhoeae, N. lactamica,* and *N. meningitidis* were diluted to various concentrations in 0.02M phosphate buffered saline containing 0.05% zwittergent and 0.05% sodium azide pH 7.5. to evaluate the sensitivity and specificity of the test system. One hundred and eight microliters of an organism dilution was reacted with 20 microliters of colloidal gold labeled antibody and 10 microliters of antibody coated latex beads. After a two minute incubation, the immunocomplexed mixture was placed on a 1.2 micron pore size cellulose acetate membrane covered with a polystyrene template having circult orifices 1.5 mm in diameter. After the liquid phase is absorbed into the membrane by diffusion, the color of the orifice was determined by the naked eye. The results are summarized in the following table:

| | Reactions* with different strains of Neisseria | | |
|---|---|---|---|
| CFU | N. gonorrhoeae | N. lactamica | N. meningitidis |
| $10^8$ | +++++ | +/− | +/− |
| $10^7$ | +++++ | +/− | +/− |
| $10^6$ | ++++ | − | − |
| $10^5$ | ++++ | − | − |
| $10^4$ | +++ | − | − |
| $10^3$ | +/− | − | − |
| $10^2$ | − | − | − |

*+ = intensity of color reaction

EXAMPLE III

Colloidal gold particle concentration immunoassay for a theophylline drug.

A theophylline conjugates were prepared by making a 8-(3-carboxypropyl)-1,3-dimethylxanthine derivative and binding this to ovalbumen (OA) and bovine serum albumen (BSA) following the procedure of Cook et al described in Res Comm Chem Path Pharm 1976 vol 13: 495. The BSA conjugate ws used to raise antisera in goats after mixing the conjugate with complete freunds adjuvant and injecting intramuscularly bimonthly.

Colloidal gold labelled theophylline OA conjugate was prepared as follows: Colloidal gold made by the reduction of chloroauric acid method described by Frens in 1973 in Nature Phys Sci 241: 20. The pH of 50 ml of colloidal gold particles having an approximate mean diameter of 20 nm and an optical density at 520 nm of 1.2 was raised to a pH of 8.8 with 0.2M potassium carbonate. Ten milligrams of theophylline OA conjugates was dissolved in 10 ml of 0.002M borax buffer and diluted to a concentration of 100 micrograms per ml. 400 micrograms of theophylline OA conjugate was mixed with the colloidal gold for 2 minutes and then 10% BSA was added to a final concentration of 1%. The colloidal gold was centrifuged at 16000 g for 30 minutes and the pellet resuspended in 0.02M Tris buffer pH 8.2 containing 1% BSA. The colloidal gold was recentrifuged and resuspended in 0.02M Tris buffer pH 8.2 containing 1% BSA and 0.05% sodium azide to a final optical density at 520 nm of 1.5

The immunoglobulin fraction of the goat anti theophylline antisera was precipitated with 40% ammonium sulphate, dissolved and dialyzed against 0.0175M phosphate buffer pH 7.0 and separated on a DEAE 52 ionic exchange resin column, equilibrated in the same buffer. The unbound protein from the column was concentrated and tested by electrophoresis for purity of immunoglobulin. The fraction was subsequently dialyzed against 0.05M borate buffer pH 8.0 and reacted with carboxylated latex particles by the same methods previously described in example I.

Theophylline drug was dissolved and serially diluted in serum and used for testing. The test for the presence of theophylline was performed as follows: 25 microliters of theophylline OA colloidal gold reagent was added to a small glass test tube containing 25 microliters of a dilution of the drug in serum. Immediately 25 microliters of the antitheophylline immunoglobulin coated solid phase particles were added and mixed. Fifty microliters of the reactants were placed on a 2.0 mm diameter orifice of a plastic laminate affixed to a 1.2 micron porous cellulose acetate membrane. An absorbant pad of filter paper was placed behind the cellulose acetate membrane to increase the flow rate. After all of the liquid passed through an orifice, the spot was examined for the absence of color which would be indicative of the presence of drug in the serum.

| Concentration of Theophylline micrograms/milliliter | Intensity of color |
|---|---|
| 0 | 3+ |
| .001 | 3+ |
| .01 | 2+ |
| .1 | N |
| 1.0 | N |
| 10.0 | N |

This methodology would be quite useful for drug screening for compliance, abuse, or toxicity, where qualitative or semiquantititative results are acceptable. The sensitivity of the assay can be controlled by varying the concentration of the reagents.

Example IV

Preparation and performance of a serological assay for the presence of an anti Group A streptococcal antibody.

The reagents in example I were used in a competitive inhibition assay using rabbit antisera to Group A streptococci and other grouping antisera to examine the feasibility of a serological assay. Group A streptococcal polysaccharide antigen was prepared by autoclaving washed Group A streptococcal organisms and recovering the supernatant after centrifugation at 10000 g for 10 minutes. The resultant extract was diluted in saline and tested in an assay by adding 25 microliters of the extract to a tube containing 25 microliters of colloidal gold labeled anti Group A streptococcal antibody, 25 microliters of anti Group A streptococcal coated solid phase particles, and 10 microliters of the normal rabbit serum. The reactants were then placed on a plastic laminate device having a 2.0 mm diameter orifice and an attached 1.2 micron pore size cellulose acetate filter. After separation the bound colloidal gold could be visualized. The serological assay was performed by diluting known antisera containing anti Group A antibodies into normal rabbit serum and then testing the diluted antisera for its ability to inhibit the aforesaid reaction. The results are summarized in the following table:

| Identification | Dilution | Reactivity |
| --- | --- | --- |
| Anti Group A | Undiluted | N |
| Anti Group A | 1:10 | N |
| Anti Group A | 1:100 | N |
| Anti Group A | 1:1000 | 1+ |
| Anti Group A | 1:10000 | 3+ |
| Anti Group C | undiluted | 3+ |

The invention has been described in detail with particular reference to preferred embodiments thereof, but it will be understood that variations and modifications can be effected within the spirit and scope of the invention.

We claim:

1. A method for detecting in a biological specimen the presence of a ligand or an antiligand selected from the group consisting of antigens, haptens, antibodies and nucleic acids, said method comprising the steps of:
   (a) adding to said biological specimen (1) a colloidal gold labeled ligand or a colloidal gold labeled antiligand and (2) solid phase capture particles coated with ligand or with antiligand;
   (b) applying the resultant of step (a) to a small zone on a porous film, said film having a minimal effective pore size smaller than (2) but greater than the size of (1), whereby the capture particles (2) are deposited on the exposed surface of the porous film; and
   (c) observing the small zone of the porous film for any color development due to (1) having become bound to (2).

2. The method of claim 1 carried in a non-competitive mode wherein a positive result is indicated by color development on the porous film.

3. The method of claim 1 carried out in a competitive mode wherein a positive result is indicated by an absence of color development on the porous film.

4. The method of claim 1, wherein a substep of adding solvent or a buffer to said capture particles after performing step (b) and prior to performing step (c).

5. The method of claim 1, wherein said capture particles have a mean diameter of from about 0.10 microns to 20.0 microns.

6. The method of claim 1, wherein said small zone on porous film having an area of from about 0.2 mm$^2$ to 30 mm$^2$.

7. The method of claim 1, wherein said colloidal gold having a mean particle diameter of from about 5 nm to 10 nm.

8. The method of claim 1, wherein the fluid phase of said resultant step (a) flows into said porous film by a process selected from the group comprised of diffusion, positive pressure, negative pressure, filtration or any combination thereof.

9. The method of claim 1, wherein the ligands or antiligands are covalently attached to said capture particles.

10. The method of claim 1, wherein the antiligand bound to said capture particles is selected from the group comprised of antibodies, lectins, receptors, DNA fragments, and RNA fragments.

11. The method of claim 1, wherein the said antiligand is a DNA or RNA fragment and the said ligand is complimentary DNA or RNA.

12. The method of claim 1, wherein step (a) has an additional substep of treating said biological speciment with a solubilizing agent selected from the group comprised of enzymes, detergents, salts, reducing reagents, and any combination thereof.

13. The method of claim 1, wherein (1) and (2) are mixed and added as a single reagent.

14. The method of claim 1, wherein the resultant of step (a) is incubated from about 1 second to 18 hours prior to performing step (b).

15. A method for detecting in a biological specimen the presence of a ligand or an antiligand selected from the group consisting of antigens, haptens, antibodies and nucleic acids, said method comprising the steps of:
   (a) applying (2) solid phase capture particles coated with ligands or with antiligands to a small zone or a porous film, said film having a minimal effective pore size smaller than said capture particles,
   (b) adding to said biological specimen (1) a colloidal gold labeled ligand or a colloidal gold labeled antiligand, said colloidal gold having a mean particle size smaller than said minimal effective pore size of said film, and
   (c) applying the resultant of (b) to the resultant of (a) and
   (d) observing the small zone of the porous film for any color development due to (1) having become bound to (2).

16. The method of claim 15 carried in a non-competitive mode wherein a positive result is indicated by color development on the porous film.

17. The method of claim 15 carried out in a competitive mode wherein a positive result is indicated by an absence of color development on the porous film.

18. The method of claim 15, wherein a substep of adding solvent or buffer to said capture particles after step (c) and prior to step (d).

19. The method of claim 15, wherein said capture particles having a mean diameter of from about 0.10 microns to 20.0 microns.

20. The method of claim 15, wherein said small zone on porous film having an area of from about 0.2 mm$^2$ to 30 mm$^2$.

21. The method of claim 15, wherein said colloidal gold having a mean particle diameter of from about 5 nm to 100 nm.

22. The method of claim 15, wherein the fluid phase of said resultant step (a) flows into said porous film by a process selected from the group comprised of diffusion, positive pressure, negative pressure, filtration or any combination thereof.

23. The method of claim 15, wherein the ligands or antiligands are covalently attached to said capture particles.

24. The method of claim 15, wherein the antiligand bound to said capture particles is selected from the group comprised of antibodies, lectins, receptors, DNA fragments, and RNA fragments.

25. The method of claim 15, wherein the said antiligand is a DNA or RNA fragment and the said ligand is complimentary DNA or RNA.

26. The method of claim 15, wherein step (a) has an additional substep of treating said biological specimen with a solubilizing agent selected from the group comprised of enzymes, detergents, salts, reducing reagents, and any combination thereof.

27. The method of claim 15, wherein the resultant of step (b) is incubated from about 1 second to 18 hours prior to performing step (c).

* * * * *

UNITED STATES PATENT AND TRADEMARK OFFICE
CERTIFICATE OF CORRECTION

PATENT NO. : 4,853,335

DATED : August 1, 1989

INVENTOR(S) : Duane A. OLSEN and David BERNSTEIN

It is certified that error appears in the above-identified patent and that said Letters Patent is hereby corrected as shown below:

Column 9
    Claim 7, line 3, change "10 nm" to --100 nm--.

Signed and Sealed this

Eleventh Day of August, 1992

Attest:

DOUGLAS B. COMER

*Attesting Officer*      *Acting Commissioner of Patents and Trademarks*